(12) United States Patent
Frederix et al.

(10) Patent No.: US 10,041,940 B2
(45) Date of Patent: Aug. 7, 2018

(54) ANALYTE DETECTION METHOD AND ANALYTE DETECTION INTEGRATED CIRCUIT

(75) Inventors: Filip Frederix, Heverlee (BE); Friso Jacobus Jedema, Eindhoven (NL); David Van Steenwinckel, Holsbeck (BE); Hilco Suy, Eindhoven (NL)

(73) Assignee: NXP B.V., Eindhoven (NL)

( * ) Notice: Subject to any disclaimer, the term of this patent is extended or adjusted under 35 U.S.C. 154(b) by 210 days.

(21) Appl. No.: 13/570,864

(22) Filed: Aug. 9, 2012

(65) Prior Publication Data
US 2013/0053268 A1 Feb. 28, 2013

(30) Foreign Application Priority Data
Aug. 22, 2011 (EP) .................................... 11178294

(51) Int. Cl.
*G01N 33/543* (2006.01)
*C12Q 1/6825* (2018.01)
*G01N 27/414* (2006.01)

(52) U.S. Cl.
CPC ....... *G01N 33/5438* (2013.01); *C12Q 1/6825* (2013.01); *G01N 27/4145* (2013.01)

(58) Field of Classification Search
CPC ........... G01N 33/5438; G01N 27/4145; C12Q 1/6825
See application file for complete search history.

(56) References Cited

U.S. PATENT DOCUMENTS

| 5,466,348 A | 11/1995 | Holm-Kennedy |
| 6,238,624 B1 | 5/2001 | Heller et al. |

(Continued)

FOREIGN PATENT DOCUMENTS

| WO | 2007/060601 A1 | 5/2007 |
| WO | 2008/132656 A2 | 11/2008 |
| WO | 2009/047703 A1 | 4/2009 |

OTHER PUBLICATIONS

"Magnetically Controlled Assays", Philips, retrieved from the Internet Aug. 3, 2012 at http://www.business-sites.philips.com/magnotech/technology/index, 1 pg. (undated, earlier than Mar. 1, 2011).

(Continued)

Primary Examiner — Melanie Yu Brown

(57) ABSTRACT

A method for providing an integrated circuit such that first and second sensing electrodes respectively have at their surfaces first and second receptor molecules for selectively binding to first and second analytes of interest; exposing the integrated circuit to a sample potentially comprising at least one of the first and second analytes, providing a first bead having a first electrical signature attached to a first molecule having a conformation/affinity for binding to the first sensing electrode dependent on the presence of the first analyte; providing a second bead having a second electrical signature attached to a second molecule having a conformation/affinity for binding to the second sensing electrode dependent on the presence of the second analyte; and determining the presence of the electrical signature of the first and/or second bead(s) on the first and second sensing electrodes respectively. An IC for implementing this method.

20 Claims, 15 Drawing Sheets

(56) References Cited

U.S. PATENT DOCUMENTS

| | | | |
|---|---|---|---|
| 6,824,669 B1 * | 11/2004 | Li | G01N 33/5438 204/403.01 |
| 7,635,420 B1 * | 12/2009 | Li | B03C 5/026 204/547 |
| 2002/0165675 A1 | 11/2002 | Golovlev | |
| 2004/0248144 A1 * | 12/2004 | Mir | C12Q 1/6818 435/6.11 |
| 2005/0003398 A1 | 1/2005 | Tao et al. | |
| 2007/0178516 A1 * | 8/2007 | Sosnowski et al. | 435/6 |
| 2008/0108164 A1 | 5/2008 | Oleynik | |
| 2010/0075340 A1 * | 3/2010 | Javanmard et al. | 435/7.1 |
| 2010/0203516 A1 * | 8/2010 | Campbell | C12Q 1/6816 435/6.11 |
| 2010/0314699 A1 * | 12/2010 | Meftah | G01N 33/5438 257/414 |
| 2011/0256634 A1 | 10/2011 | Jedema | |
| 2014/0015548 A1 * | 1/2014 | Naughton | G01R 27/26 324/658 |

OTHER PUBLICATIONS

Extended European Search Report for EP Patent Appln. No. 11178294.2 (Mar. 6, 2012).

Wright, Aaron T; "Differential receptor arrays and assays for solution-based molecular recognition"; Chemical Society Reviews (Jan. 31, 2006).

Office Action dated Jan. 26, 2016, for European Patent Application No. 11 178 294.2, 5 pages.

Wikipedia, "ELISA", http://en.wikipedia.org/wiki/ELISA, last retrieved Jan. 11, 2018.

Perez et al., "Viral detection using DNA functionalized gold filaments," https://www.researchgate.net/publication/44579271, Aug. 2009, 16 pages.

Steichen et al,, "Interfacial Behavior of a Hairpin DNA Probe Immobilized on Gold Surfaces," http://pubs.acs.org/, Apr. 16, 2009, 7 pages.

Kim et al., "Molecular Beacons in Biomedical Detection and Clinical Diagnosis," http://www.ijcep.com/, Aug. 24, 2007, 12 pages.

Fan et al., "Electrochemical interrogation of conformational changes as a reagentless method for the sequence-specific detection of DNA," PNAS, vol. 100, No. 6, Aug. 5, 2003, 4 pages.

Public Health Research Institute, New Jersey Medical School at Rutgers, "Molecular Beacons", http://www.molecular-beacons.org/, last retrieved Jam. 11, 2018.

\* cited by examiner

ANALYTE DETECTION METHOD AND ANALYTE DETECTION INTEGRATED CIRCUIT

CROSS-REFERENCE TO RELATED APPLICATIONS

This application claims the priority under 35 U.S.C. § 119 of European patent application no. 11178294.2, filed on Aug. 22, 2011, the contents of which are incorporated by reference herein.

FIELD OF THE INVENTION

The present invention relates to a method of detecting an analyte of interest, comprising providing a plurality of individually addressable sensing electrodes including a first sensing electrode comprising at its surface a first receptor for selectively binding to a first analyte of interest and a second sensing electrode comprising at its surface a second receptor for selectively binding to a second analyte of interest.

The present invention further relates to an integrated circuit (IC) comprising a plurality of individually addressable sensing electrodes including a first sensing electrode comprising at its surface a first receptor for selectively binding to a first analyte of interest and a second sensing electrode comprising at its surface a second receptor for selectively binding to a second analyte of interest.

The present invention yet further relates to a method of functionalizing such an IC.

BACKGROUND OF THE INVENTION

A biosensor may be denoted as a device which may be used for the detection of an analyte that combines a biological component with a physicochemical or physical detector component.

For instance, a biosensor may be based on the phenomenon that capture molecules immobilized on a surface of a biosensor may selectively hybridize with target molecules in a fluidic sample, for instance when an antibody-binding fragment of an antibody or the sequence of a DNA single strand as a capture molecule fits to a corresponding sequence or structure of a target molecule. When such hybridization or sensor events occur at the sensor surface, this may change the electrical properties of the surface and the volume directly above the surface which can be detected as the sensor event.

Many suitable specific binding pair candidates are known per se, which are typically based on a lock-and-key type interaction between a receptor molecule and a molecule, e.g. a drug. This makes a sensing apparatus such as an assay-based apparatus particularly suitable to determine the presence or absence of specific proteins and other biological compounds such as DNA, RNA, hormones, metabolites, drugs and so on, or to determine the activity and function of active and catalytic biomolecules such as proteins, peptides, prions, enzymes, aptamers, ribozymes and deoxyribozymes. For instance, immunoassays are already used to determine the specific amount of specific proteins in body fluids to aid further diagnosis and treatment.

Due to advances in semiconductor technology, it has become feasible to detect single capture events on a sensing surface of such sensors. An example of such a sensor is disclosed in PCT patent application WO 2009/047703, in which a capture molecule forms an insulating layer of a capacitor, with the plates or sensing electrodes of the capacitor formed by a conductive sensing surface and a fluid sample respectively. A capture event causes a change in the dielectric constant of the insulating layer including the volume directly above the sensor surface in which a capture event takes place, which affects the capacity of the capacitor. The change in capacitance can be measured, e.g. as a bias on a current through a transistor, as is the case in this application.

An alternative arrangement is disclosed in PCT patent application WO 2008/132656, in which an extended gate field effect transistor is disclosed with capture molecules on the surface of the extended gate as the sensing electrode, such that the gate potential of the transistor can be altered by capture events.

Another type of biosensor that has been gaining considerable attention is an assay-type biosensor in which antibodies are bound to magnetic beads, which are attracted to a sensing surface carrying further antibodies by a magnetic force, with the analyte of interest binding the magnetic beads to the sensing surface by forming a binding pair with the antibodies and the further antibodies. Examples of such assays are for instance given in PCT patent application WO 2007/060601, although the biosensors based on such magnetic beads are less suitable for detection at single binding event resolution. Instead, a bulk magnetic signal is detected which has a magnitude that scales with the concentration of the analyte of interest in the investigated sample.

As is for instance disclosed in WO 2008/132656 and WO 2009/047703, it is possible to functionalize different parts of the array of biosensors with different receptor molecules such that different analytes can be detected in parallel. This is of course attractive, as it reduces the overall detection times for different analytes. However, the diversification of the functionalization of the different biosensors on the IC is not trivial due to the small sensing area of the most advanced CMOS biosensors. In order to be able to detect a specific binding event, it must be known which biosensor elements, e.g. electrode or electrodes, contains which receptor molecule. This therefore requires careful placement of the receptor molecules on the electrodes, which may be achieved by spotting techniques for instance, in which a droplet or spot of a solution that contains a specific receptor is placed on a selected part of the biosensor surface.

However, modern manufacturing techniques facilitate the provision of ICs that comprise biosensor arrays, e.g. arrays of electrodes that have a pitch substantially smaller than the size of such droplets, such that standard spotting techniques are unsuitable for providing individual electrodes with separate receptors. For instance, it is routinely possible to provide an area of a few hundred microns squared whereas the diameter of a single spot as provided by common spotting techniques is typically in the region of 100-300 microns, i.e. several orders too large to address individual electrodes which sizes are in the 100 nm range. These kinds of spot sizes are in the same order of magnitude than the full sensor array which would not allow to deposit different spots on one biosensor. Smaller spots may be provided e.g. by using atomic force microscope (AFM)-like tip spotting techniques such as the commercial systems of BioForce or Nanodrop, but the cost of such techniques is prohibitive for large scale industrial application. Moreover, such sensor functionalization typically takes place in a biological laboratory, where such advanced spotting technologies may not be available.

Apart from the above functionalization problems, a further problem associated with such biosensor arrays is that the single molecule detection signal typically is rather weak, such that long acquisition times may be required to achieve an acceptable signal to noise ratio.

SUMMARY OF THE INVENTION

The present invention seeks to provide a method facilitating the simultaneous detection of different analytes of interest using an IC comprising a plurality of sensing electrodes that overcomes at least some of the aforementioned problems.

The present invention further seeks to provide an IC comprising a plurality of sensing electrodes capable of improved simultaneous detection of different analytes of interest.

According to an aspect of the present invention, there is provided a method of functionalizing an integrated circuit comprising an exposed surface carrying a plurality of sensing electrodes, the method comprising providing a solution comprising a plurality of biomolecule receptor molecules for selectively binding to different analytes of interest; and exposing said surface to said solution, thereby forming a random distribution of said receptor molecules on the respective sensing electrodes.

The present invention is based on the realization that in combination with a novel detection technique (vide infra), it is no longer necessary to have a priori knowledge of the location of a particular type of receptor molecule on the array of electrodes. Consequently, the use of spotting techniques may be obviated altogether, thereby significantly reducing the complexity of the functionalization of the individual biosensor elements, e.g. the individual sensing electrodes.

In accordance with a further aspect of the present invention, there is provided a method of detecting an analyte of interest, comprising providing a functionalized integrated circuit in accordance with the functionalization method of the present invention such that a first sensing electrode comprises at its surface a first receptor molecule for selectively binding to a first analyte of interest and a second sensing electrode comprises at its surface a second receptor molecule for selectively binding to a second analyte of interest; exposing said functionalized integrated circuit to a sample potentially comprising at least one of the first analyte and the second analyte, providing a first bead having a first electrical signature attached to a first molecule having a conformation or an affinity for binding to the first sensing electrode that is dependent on the presence of the first analyte in said sample; providing a second bead having a second electrical signature attached to a second molecule having a conformation or an affinity for binding to the second sensing electrode that is dependent on the presence of the second analyte in said sample; and determining the presence of the electrical signature of the first bead and/or the second bead on the first electrode and the second electrode respectively.

The detection method of the present invention is based on the insight that by using beads that have a electrical signature that is designed to be characteristic for a particular type of analyte of interest, the analyte of interest may be detected in a sample by the occurrence (or disappearance) of this signature somewhere on the array (plurality) of sensing electrodes. This at the same time will disclose which electrodes of the array have been functionalized with a receptor molecule forming the binding pair involving this analyte of interest in the random distribution step of the functionalization method of the present invention.

The different electrical signatures may be achieved in any suitable manner. Preferably, the first bead and the second bead have different sizes and/or are made of different materials to achieve such different electrical signatures, e.g. different capacitive signatures.

The first molecule and the second molecule may be comprised in said sample. For instance, the first molecule has an affinity for binding to the first receptor molecule and the second molecule has an affinity for binding to the second receptor molecule. The first and second molecules may for instance be antibodies or the like that selectively bind to the analyte of interest, e.g. as part of a sandwich assay.

In an alternative embodiment, the binding event may be based on a replacement assay, in which case the method further comprises the steps of forming respective binding pairs between the first receptor molecule and the first molecule and between the second receptor molecule and the second molecule prior to exposing said array to said sample; and replacing the first molecule with the first analyte and/or replacing the second molecule with the second analyte in said binding pairs following exposure of the array to said sample. In this embodiment, the binding event is detected by the disappearance of the electrical signature from the sensing electrode as the first molecule having the bead attached to it is replaced with the analyte of interest at the surface of the electrode.

In yet another embodiment, the first molecule is the first receptor molecule and the second molecule is the second receptor molecule, and wherein the first receptor molecule adopts a hairpin confirmation in the absence of the first analyte of interest, and the second receptor molecule adopts a hairpin confirmation in the absence of the second analyte of interest. This is for instance a suitable embodiment in the field of DNA recognition, where the complementary base pair sequence, typically adopts a hairpin or folded conformation, which is disrupted upon the formation of a binding pair with a complementary DNA sequence. This moves the bead at the end of the receptor molecule away from the surface of the sensing electrode, which can be detected by a change in the capacitance. The amount of change will at least in part depend on the electrical signature of the bead.

In a further embodiment, the first bead and the second bead are magnetic beads. This may for instance be utilized in that the step of electrically detecting the presence of the first bead and/or the second bead on the first sensing electrode and the second sensing electrode respectively may comprise providing at least the first sensing electrode and the second sensing electrode with an oscillating electromagnetic field having a time-variable frequency; and detecting a frequency-dependent capacitive signal indicative of the presence of a bead of a particular size on each of said sensing electrodes. Hence, the different electrical signature of the beads as caused by the different sizes, different materials and/or weights of the beads will cause each bead to resonate in the applied electromagnetic field until it reaches a critical frequency that is specific to the particular electrical signature of the bead. Above this frequency, the bead will no longer be able to follow the altering electromagnetic field, which can be detected as a change in the time-dependent capacitance of the dielectric above the sensing electrode, i.e. the detected signal will no longer be modulated with the applied electromagnetic field frequency. Hence, the detection of the critical resonance frequency for each electrode will establish which bead, and therefore which analyte of interest, has bound to the (a priori unknown) receptor molecule on the sensing electrode.

In accordance with yet another aspect of the present invention, there is provided an integrated circuit comprising a plurality of individually addressable sensing electrodes and a signal processor individually coupled to the respective sensing electrodes, the signal processor being adapted to identify a specific binding event of a particular analyte of interest on one of said sensing electrodes based on a electrical signature of a bead involved in said binding event. Such an IC facilitates the parallel detection of different analytes of interest on different sensing electrodes without the need for a priori knowledge of which receptor molecule has been placed, i.e. immobilized on which electrode.

In an embodiment, the integrated circuit is a functionalized IC, wherein the respective electrodes comprise a random distribution of different receptor molecules.

The integrated circuit may further comprise a field generator for applying an oscillating electromagnetic field having a time-variable frequency to the plurality of sensing electrodes, wherein the signal processor is adapted to identify an analyte of interest by way of the resonance characteristics of the bead involved in its binding reaction in said oscillating electromagnetic field.

. . .

BRIEF DESCRIPTION OF THE EMBODIMENTS

Embodiments of the invention are described in more detail and by way of non-limiting examples with reference to the accompanying drawings, wherein:

FIG. 1 schematically depicts a prior art sensor device;

FIG. 2 schematically depicts an electrical replacement model of the prior art sensor device;

FIG. 3 schematically depicts an IC having a sensing array that has been functionalized using a spotting technique;

FIG. 4 schematically depicts a sensing electrode model;

FIG. 5 schematically depicts the dependence of an electrical signal of such a sensing electrode to the distance of a bead over this electrode;

FIG. 6 schematically depicts an embodiment of a detection method of the present invention;

FIG. 7 schematically depicts a sensing signal obtained with the detection principle of FIG. 6;

FIG. 8 schematically depicts an embodiment of another detection method of the present invention;

FIG. 9 schematically depicts an embodiment of yet another detection method of the present invention;

FIG. 10 schematically depicts an IC having a sensing array that has been functionalized in accordance with an aspect of the present invention;

FIG. 11 schematically depicts an embodiment of an IC according to the present invention;

FIG. 12 schematically depicts an embodiment of another IC according to the present invention;

FIG. 13 schematically depicts an operating mode of the IC of FIG. 12;

FIG. 14 schematically depicts a plurality of electrical signals that can be obtained in the operating mode of FIG. 13.

Figure 21:
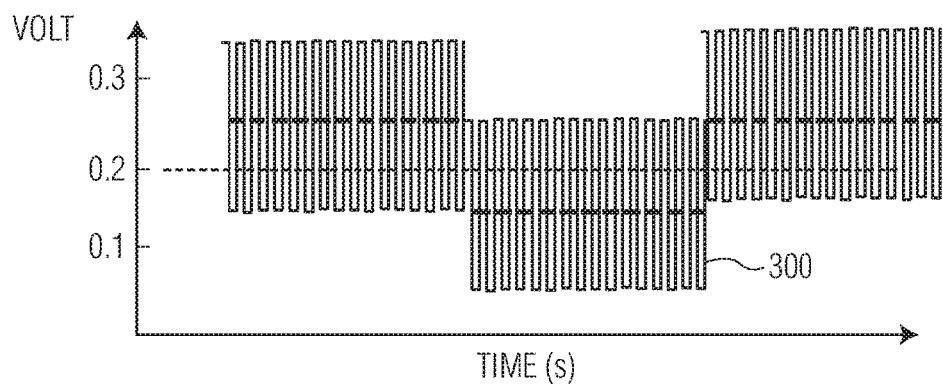
Figure 22:
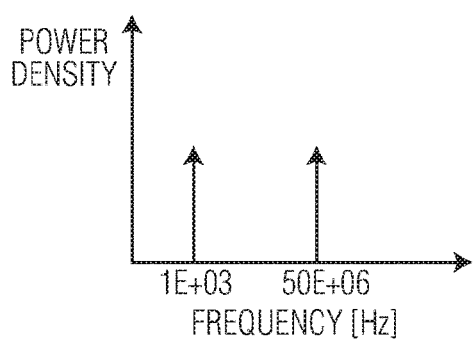
Figure 23:
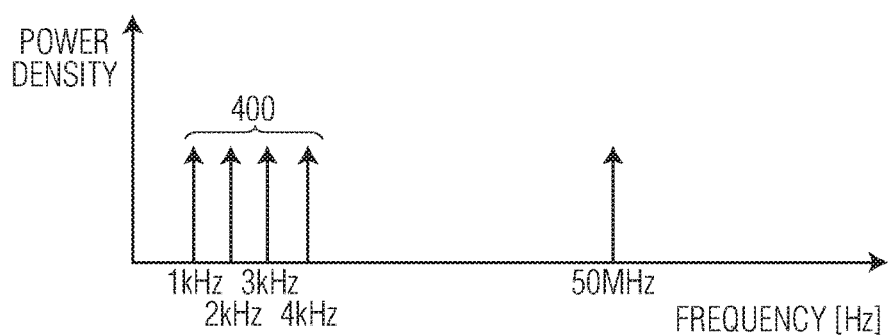

FIG. 21 schematically depicts an exemplary control signal for the sensing electrodes of the IC of the present invention;

FIG. 22 schematically depicts the modulation frequencies of the exemplary control signal of FIG. 21; and FIG. 23 schematically depicts an embodiment of the bead detection principle of the present invention.

DETAILED DESCRIPTION OF THE DRAWINGS

It should be understood that the Figures are merely schematic and are not drawn to scale. It should also be understood that the same reference numerals are used throughout the Figures to indicate the same or similar parts.

Figure 1:
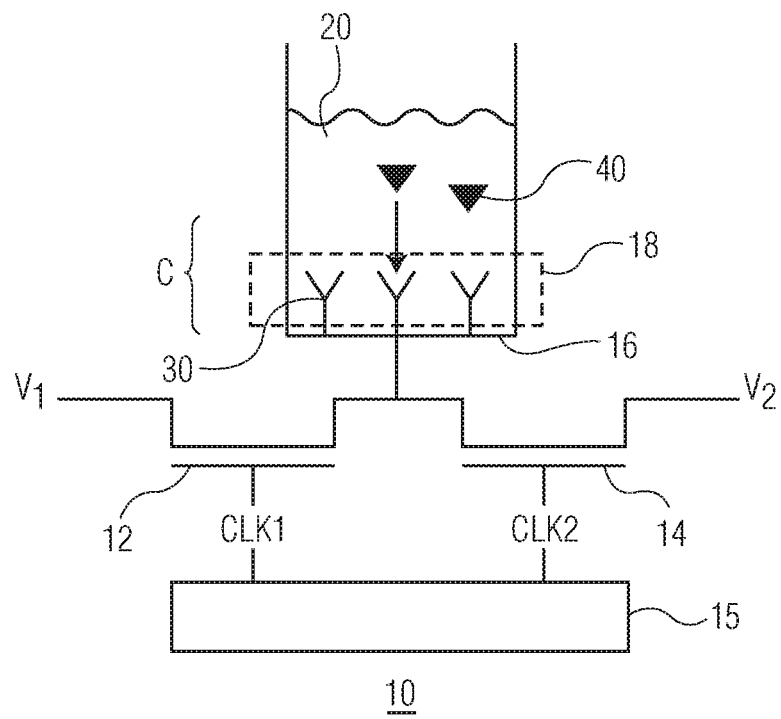

FIG. 1 depicts an embodiment of the sensor device 10 of WO 2009/047703. The sensor device 10 comprises a first transistor 12 and a second transistor 14 coupled in series between a first voltage source $V_1$ and a second voltage source $V_2$ such as the supply voltage and ground respectively. The first transistor 12 and the second transistor 14 are controlled by respective control signals CLK1 and CLK 2 from a control circuit 15, e.g. a clock signal generator.

A node in the source/drain connection between the first transistor 12 and a second transistor 14 is connected to an electrode 16 carrying a number of capture molecules 30 for capturing an analyte of interest 40 from a sample 20. The electrode 16 and the sample 20 form the capacitor plates of a capacitor C, which are separated by a dielectric layer 18 formed by the one or more capture molecules 30.

In operation, the capacitor C is charged by connecting the electrode 16 to voltage source $V_1$ through the first transistor 12. The subsequent occurrence of a capture event, i.e. the formation of a binding pair between a capture molecule 30 and a molecule of the analyte of interest 40 induces a change in the dielectric constant of the dielectric layer 18, thus affecting the capacitance of the capacitor C. Hence, upon read-out of the capacitor C by switching the first transistor to a non-conductive state whilst switching the second transistor 14 to a conductive state, the change in capacitance can be derived from the charge flowing from the electrode 16 to the second voltage source $V_2$.

The changes in the dielectric constant of the dielectric layer 18 are typically affected by changes in the surface potential as well as a volumetric contribution to the dielectric constant, as will be explained in more detail with the aid of FIG. 2.

Figure 2:
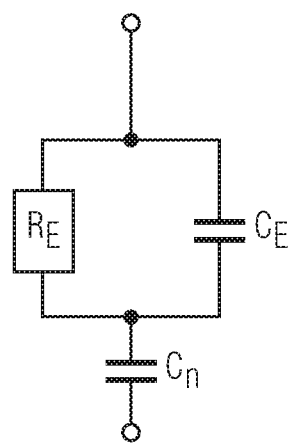

To elaborate some more: the signal (S) of the sensor 10 is a function of 3 impedances, as shown in FIG. 2. Each impedance is sensitive to an approaching analyte particle, i.e., as shown in equation (1):

$$S=S(C_n, R_E, C_E) \qquad (1)$$

The electrode capacitance $C_n$, the electrolyte resistance $R_E$ and the electrolyte capacitance $C_E$ are all determined by the geometrical size of the sensor electrode. In the absence of an analyte particle, these impedances may be expressed as shown in equations (2)-(4):

$$C_n = c_0 \pi \left(\frac{d}{2}\right)^2 \qquad (2)$$

$$R_E = \frac{16}{3\pi^2 d} \frac{1}{\sigma_E} \qquad (3)$$

$$C_E = \frac{3\pi^2 d}{16} \varepsilon_0 \varepsilon_E \qquad (4)$$

Here, d is the diameter of the electrode, $c_0$ is the capacitance density of the dielectric layer 18, e.g. a thiolated SAM or thiolated DNA hybridization probes, $\sigma_E$ is the dc resistivity of the electrolyte, $\varepsilon_o$ is the permittivity in vacuum (8.854× $10^{-12}$ C/V-m) and $\varepsilon_E$ is the relative permittivity of the electrolyte solution. Typical numbers would be d=130 nm for PT2, $c_0$=0.01 F/m² for a thiolated SAM, $\sigma_E$=1.57 S and $\in_E$=75.4 for a 150 mM Phosphate Buffered Solution comprising 2 g NaCl, 0.2 g KCl, 0.2 g Na$_2$HPO$_4$ and 0.2 g KH$_2$PO$_4$ in 1 liter deionized water, yielding typical numbers for $C_n$=133 aF, $C_{E,0}$=160 aF and $R_{E,0}$=2.6 MΩ for the nano electrode in physiological solutions. Note that the impedances of equations (2)-(4) can be considered as the fundamental impedances relevant for the (bio)sensor 10. These impedances are affected in the presence of an analyte particle or biomolecules in the (near) proximity of the electrode surface.

The biosensor element of FIG. 1 is a non-limiting example of a suitable sensor element for an IC comprising sensor array formed by a plurality of individually controllable capacitive sensing electrodes 16. Other embodiments of such sensing electrodes, such as the sensing elements disclosed in WO 2008/132656, are equally feasible. It should be understood that the scope of the present invention is not particularly limited to a specific type of capacitive sensing element; any sensing element suitable for integration into an IC and capable of detecting individual specific binding events can be used in the context of the present invention.

Figure 3:
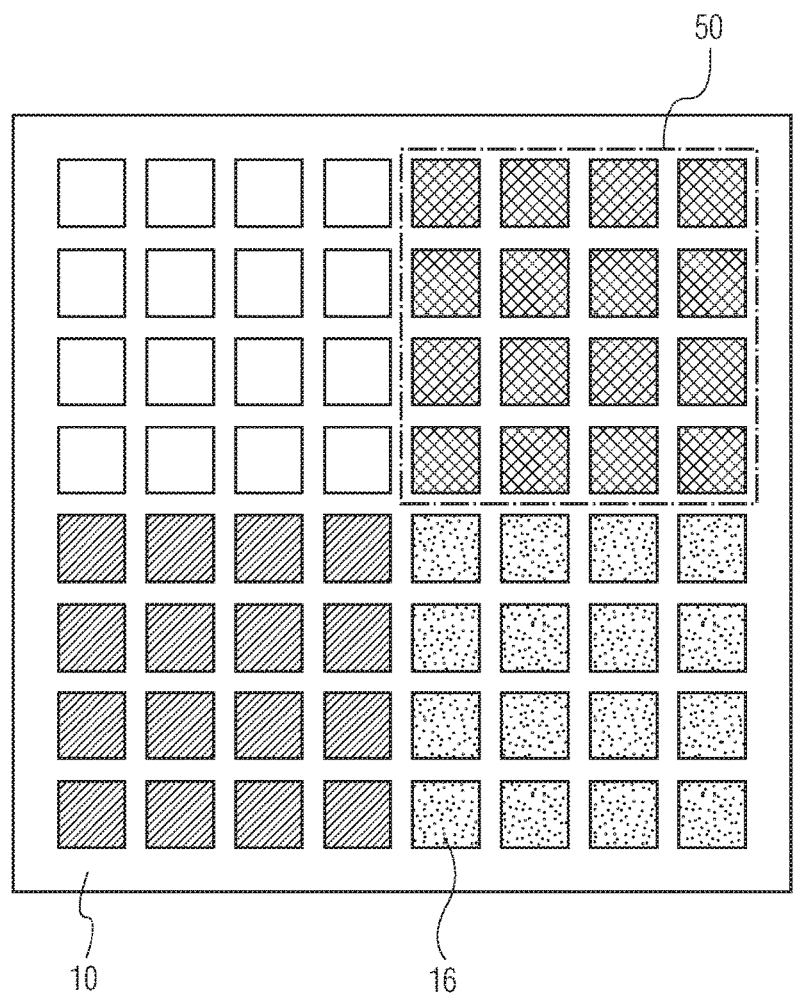

As previously mentioned, the array of sensing electrodes disclosed in e.g. WO 2008/132656 and WO 2009/047703 can be functionalized to simultaneously detect multiple analytes of interest, thereby providing a powerful lab-on-chip solution. FIG. 3 depicts a prior art solution of such a functionalization, in which a surface of an IC 10 carries a plurality of suitable sensing electrodes 16 organized in a two-dimensional array or grid. The electrodes 16 have a square shape by way of non-limiting example only; the electrodes 16 may have any suitable shape, e.g. a circular shape.

Four areas 50 can be recognized in the array, which represent distinct areas that are functionalized with a particular type of receptor molecule, with the sensing electrodes 16 in each area 50 carrying a different receptor such that the IC 10 is capable of simultaneously detecting four different types of analytes of interest in the four different sensing areas 50.

The formation of the functionalized areas 50 may be achieved using well-known spotting techniques, in which a droplet of a solution containing the desired receptor molecule is deposited on the designated area. The diameter of the droplet is typically several hundred microns, whereas modern IC manufacturing processes make it feasible to produce sensing electrodes 16 that have submicron dimensions (for this reason such electrodes are sometimes referred to as nanoelectrodes) such that it cannot be avoided, at least when using simple spotting techniques, that a large number of sensing electrodes 16 will be covered by the same receptor molecule. Hence, an IC 10 that has been functionalized using such spotting techniques can be easily recognized by the fact that areas 50 of the sensing array of the IC 10 have been homogeneously functionalized, i.e. all the sensing electrodes 16 within such an area 50 carry the same receptor molecule.

It is noted that the functionalization of electrode surfaces with such receptors is well-known per se. Many suitable procedures, e.g. the formation of a self-assembled monolayer on the surface of a sensing electrode 16 to which the receptor is bound, are readily available to the skilled person, such that this aspect of the present invention is not explained in further detail for the sake of brevity.

The aforementioned spotting techniques can be problematic. Firstly, the spotting process is time-consuming due to the need to carefully align the IC 10 with the spotting device, e.g. an inkjet print head and the need to apply several washing steps in the spotting process. The careful alignment is for instance necessary to ensure that the intended sensing electrodes 16 are being functionalized, as in order to be able to accurately detect the presence of a particular analyte of interest from a group of analytes that the IC 10 is capable of detecting, it is necessary to know a priori which receptor molecule 30 has been attached to the surface of the sensing electrode 16.

Moreover, standard spotting techniques cannot be used for an IC 10 having micron or submicron dimensions. For instance, the applicant is capable of producing an IC having a sensing array comprising overall dimensions of only a few hundred microns squared, for which differentiation of the sensing functionality becomes impossible to achieve with such standard spotting techniques as a single spot or droplet would cover the complete sensing array.

The present inventors have solved this problem based on the following realization. It is known per se to provide particles or beads as labels in assay forming reactions, as for instance is explained in detail in WO 2007/060601. The present inventors have realized that such beads can be detected capacitively using capacitive sensing electrodes 16. Furthermore, the present inventors have realized that by choosing different types of beads for different types of specific binding pairs, i.e. the (in)direct binding of a specific analyte of interest 40 to its matching receptor molecule 30, the formation of the specific particular binding pair may be detected by means of the specific electrical signature of the bead that is involved in the formation of this specific binding pair.

By providing a plurality of beads that have different electrical signatures, and associating different beads with different binding pairs, it is no longer necessary to have a priori knowledge of the location of a receptor molecule 30 on a particular sensing electrode 16, as the detection of the electrical signature that is unique to a particular specific binding event can be used to identify the presence of a particular analyte of interest. In other words, the analyte of interest is no longer detected by means of the detection of a signal at a specific position in the array of sensing electrodes 16, but is instead detected by a unique capacitive signal, which may occur at any position within this array.

To this end, each sensing electrode 16 must be capable of detecting an individual bead and its electrical signature. Different electrical signatures can be achieved by varying the dimensions and/or the materials used for the different beads. This can be understood from the following equation (5):

$$\Delta Y_E = 4\pi a^3 (\sigma_E + j\omega \varepsilon_E) \frac{\sigma_B - \sigma_E + j\omega \varepsilon_0 (\varepsilon_B - \varepsilon_E)}{2\sigma_E + \sigma_B + j\omega \varepsilon_0 (2\varepsilon_E - \varepsilon_B)} \frac{|\vec{E}_{E,0}(\vec{r}_P)|^2}{|V|^2} \quad (5)$$

This model represents an electrolyte admittance change $\Delta Y_E$ caused by insertion of a bead with radius a, dc conductivity $\sigma_B$ and permittivity $\in_B$, at position $\vec{r}_P$ into an electrolyte with DC conductivity $\sigma_E$ and permittivity $\in_E$. Here ω is the (harmonic) angular frequency, $\vec{E}_{0,E}(\vec{r}_P)$ is the local electric field in the electrolyte at the particle location before insertion of the particle, and V is the average voltage at the SAM-electrolyte interface of the nano electrode (assuming that the counter electrode is at zero voltage). It can be observed from equation (5) that the signal magnitude multiplexing can be induced by 3 parameters: its volume ($4\pi a^3$), its electrical conductivity ($\sigma_B$) and its electrical permittivity ($\in_B$).

Figure 4:
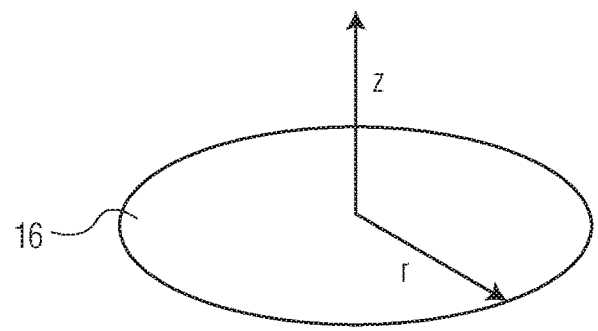
Figure 5:
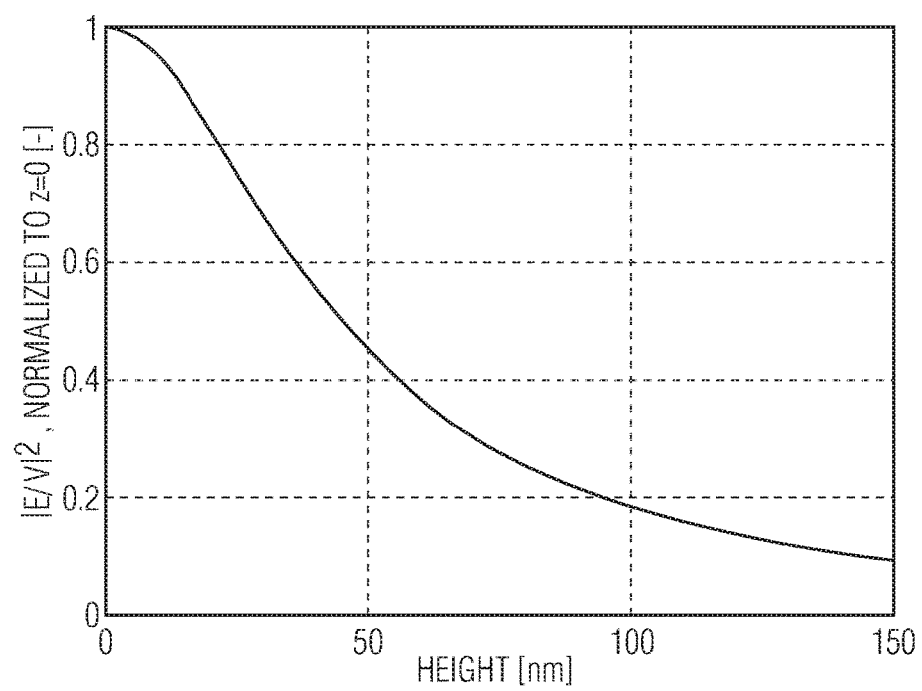

FIG. 4 depicts a circular sensing electrode having a typical electrode radius r of 75 nm, and FIG. 5 depicts the ratio $(E/V)^2$ at the centre of the circular sensing electrode as a function of the height z above the sensor, normalized at z=0. As can be seen from equation (5), the capacitance change is directly proportional to the volume of the particle or bead and its dielectric properties, relative to the medium.

Given the fact that beads typically have a substantially bigger size when compared to biomolecules (roughly 10-100-fold bigger), and the possibility to select or tune their material properties, beads or labels provide advantages to increase the signal, such that in addition to being able to avoid spotting techniques for the diversification of the functionality of the sensing electrodes 16 of the IC 10, a further advantage is that an improves signal strength can be obtained, which not only aids in differentiating between different electrical signatures, but also reduces the acquisition time of a sensing experiment.

Figure 6:
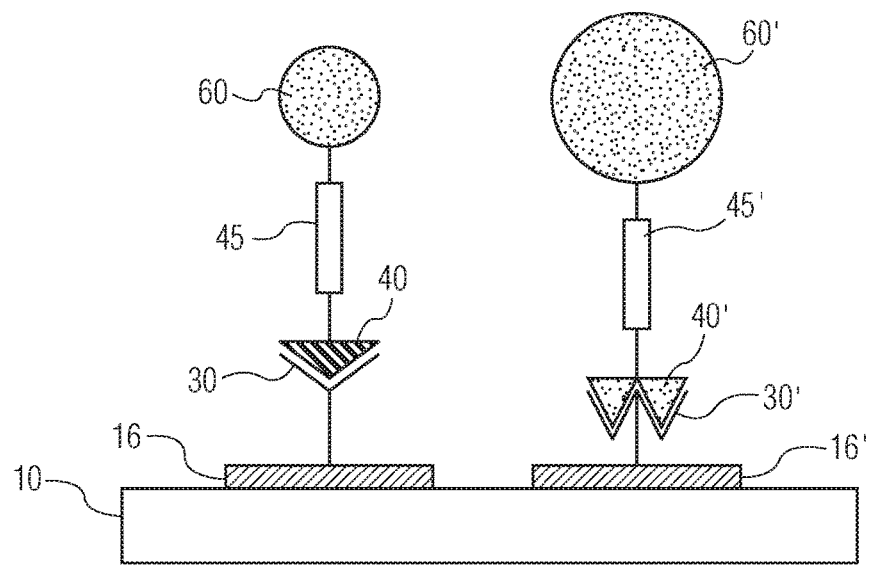

FIG. 6 shows an example embodiment of the present invention, which is based on the principle of a sandwich (or ELISA) assay. An IC 10 may comprise a plurality of sensing electrodes 16, 16'. Two electrodes are shown by way of non-limiting example and for the sake of clarity only. The electrodes 16, 16' carry different receptor molecules 30, 30'. The receptor molecule 30, e.g. an antibody, a complementary DNA strand and so on, is capable of forming a specific binding pair with analyte of interest 40, whereas receptor molecule 30', which is different to the receptor molecule 30, is capable of forming a specific binding pair with another analyte of interest 40'.

The analyte of interest 40 is capable of forming another specific binding pair with a further molecule 45, e.g. another receptor, to which a bead 60 is attached as a label. The analyte of interest 40' is capable of forming another specific binding pair with a further molecule 45', e.g. another receptor, to which a bead 60' is attached as a label. The beads 60 and 60' have different electrical signatures, i.e. influence the capacitance of the capacitive sensing elements of the IC 10 including the sensing electrode 16 and 16' respectively in a different and detectable manner, such that the specific binding event of an analyte of interest such as analytes of interest 40 and 40' can be detected by way of this electrical signature.

Figure 7:
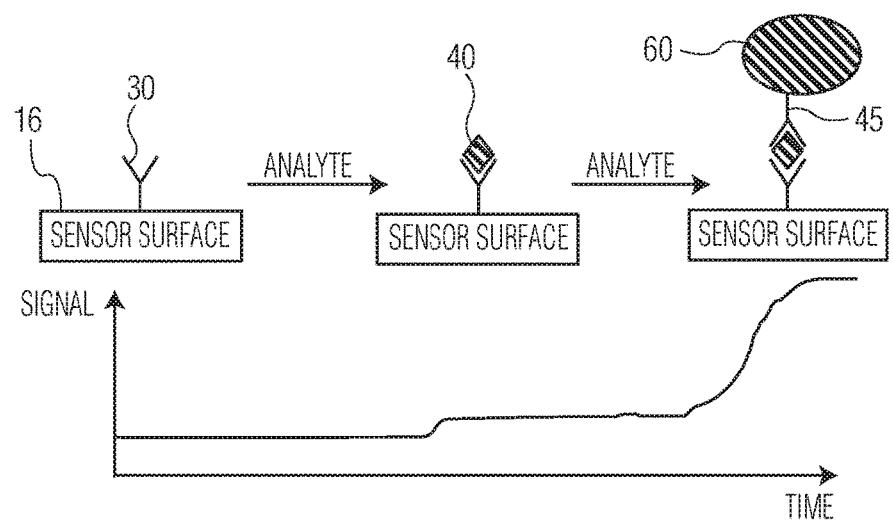

A simplified representation of the sensor signal derived from the sensing electrode 16 as a function of the analyte of interest 40 binding to the receptor molecule 30 and the binding of the further molecule 45 including bead 60 to the analyte of interest 40 is shown in FIG. 7. This demonstrates that a large increase in the intensity of the signal is obtained when the further molecule 45 including the bead 60 binds to the analyte of interest 40, thereby significantly affecting the capacitance of the capacitive sensor including the sensing electrode 16 by way of a significant change in the properties of the dielectric in between the capacitor plates as previously explained.

In FIG. 6, the different electrical signatures have been achieved by choosing different radii for the beads 60 and 60'. It should be understood that differences in electrical signature between different beads may be achieved in any suitable manner, for instance by using materials having different dielectric constants, a combination of different materials in a single bead, e.g. a bead formed of a core with a cladding or shell, in which the core and cladding or shell materials may be individually varied, a combination of different size beads and different bead materials and so on. In an embodiment, the beads 60 and 60' are polystyrene beads comprising iron grains. Such beads are commercially available from the Ademtech company. Alternatively, the beads 60 and 60' may be metallic beads such as gold beads, silver beads and so on, or the beads may comprise a dielectric material, e.g. polystyrene, polypropylene, silicon dioxide and so on. Other suitable materials for the beads that establish a sufficient electrical contrast to the medium of the sample, e.g. water, will be apparent to the skilled person.

Figure 8:
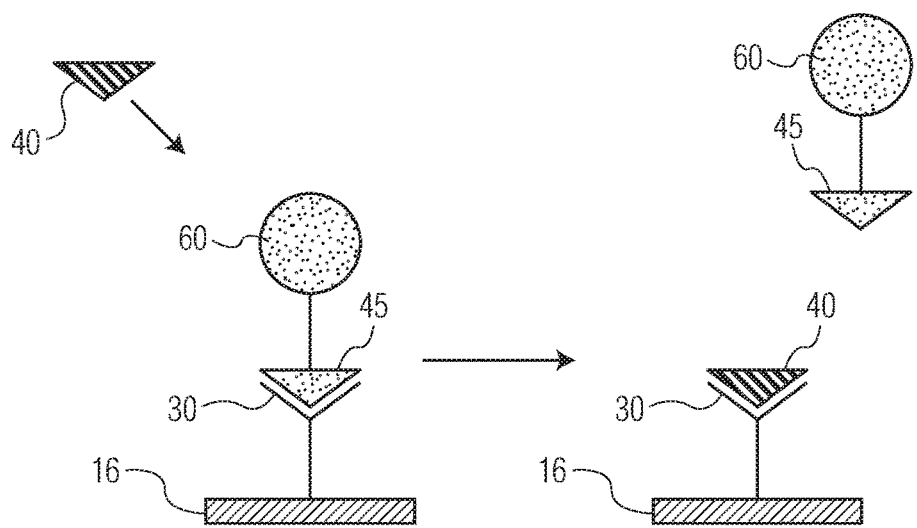

The present invention is not limited to sandwich assays. Any suitable type of assay may be used in conjunction with the embodiments of the present invention. For instance, FIG. 8 shows an alternative embodiment, which depicts a replacement assay. In this embodiment, a bead 60 bound to a further molecule 45 is bound to a matching receptor 30 prior to exposure of the IC 10 to the sample potentially comprising the analyte of interest 40, as shown on the left in FIG. 8. Upon exposure to the analyte of interest 40 as shown on the right in FIG. 8, the further molecule 45 including the bead 60 is expelled from the receptor molecule 30 and replaced by the analyte of interest 40, such that the formation of the specific binding pair between the analyte of interest 40 and the receptor molecule 30 leads to the removal of the bead 60 from the sensing electrode 16, which can be detected by a disappearance of its electrical signature, thereby signaling the specific binding event between the analyte of interest 40 and the receptor molecule 30. By utilizing different receptor molecules 30 on different sensing electrodes 16 in combination with beads having different electrical signatures for the different receptor molecules, different analytes of interest can be simultaneously detected by the disappearance of the respective characteristic electrical signatures from the various sensing electrodes 16. Other types of assays, e.g. competitive assays, may also be employed. In the above examples, the beads 60 and 60' have been attached to a molecule that interacts with the analyte of interest. Alternatively, the various analytes of interest may be directly labeled with the beads 60 and 60'.

Figure 9:
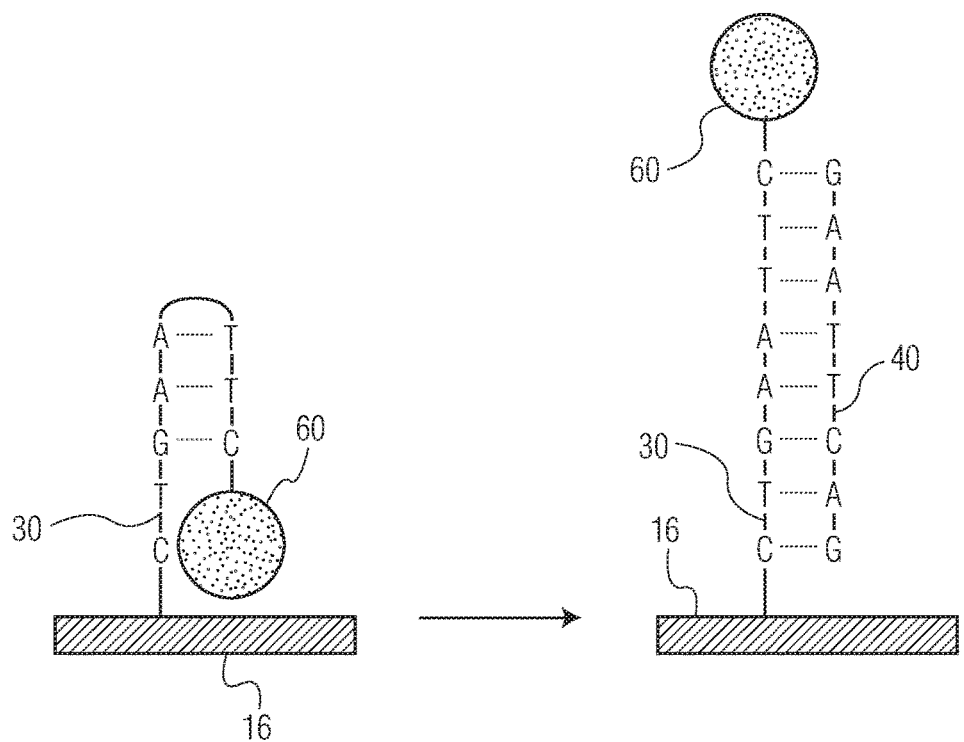

The principles of the present invention are not limited to assay-based analyte detection. FIG. 9 shows an alternative embodiment in which a bead 60 is attached to a receptor molecule 30 on the surface of the sensing electrode 16. In this embodiment, the receptor molecule 30 forms a molecular beacon, e.g. a DNA hairpin as shown on the left in FIG. 9, in which the receptor molecule adopts an internally folded conformation, thus bringing the bead 60 to a first distance away from the surface of the sensing electrode 16.

Upon engaging in a specific binding event with an analyte of interest 40, e.g. a complementary DNA strand as shown on the right in FIG. 9, the receptor molecule changes its conformation by unfolding into a more linear or stretched conformation, which causes the migration of the bead 60 to a new location over the sensing electrode 16 at a different distance to the sensing electrode 16 compared to the first distance. This causes a change in the capacitance over the sensing electrode 16 with the magnitude of the change being governed by the electrical signature of the bead 60.

Hence, the use of different beads 60 having different electrical signatures in conjunction with different types of receptor molecules 30 on the respective sensing electrodes 16 of the IC 10 will allow for the simultaneous detection of the different analytes of interest by way of the various capacitance changes induced by the unfolding of the different receptor molecules 30 upon forming the specific binding pair with the matching analyte of interest.

The surface of the IC 10 comprising the plurality of sensing electrodes 16 may be functionalized by exposing the surface to a sample comprising the desired plurality of receptor molecules 30, 30'. This causes a random distribution of receptor molecules over the sensing electrodes 16. This is schematically depicted in FIG. 10.

The resulting functionalized IC 10 can be easily distinguished from prior art ICs in which spotting techniques have been used to differentiate the functionalization of the array of sensing electrodes 16 as the differentiated IC of the present invention displays a random, i.e. unordered, distribution of the various receptor molecules 30 over the surface of the respective sensing electrodes 16, whereas in the prior art IC a high degree of order (grouping in regions as explained in the detailed description of FIG. 3) is present.

Figure 10:
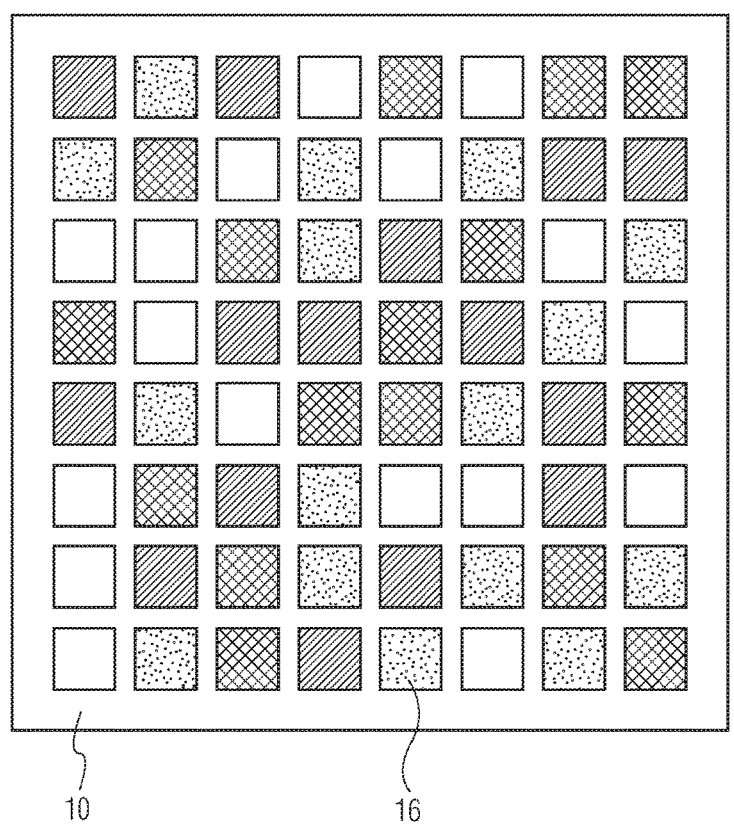

It should be understood that FIG. 10 provides a simplified representation of the resulting IC 10. In reality, most sensing electrodes will comprise more than one type of receptor molecule 30, as well as some sensing electrodes 16 not being functionalized at all. This, however, is not a problem, as the presence of multiple types of receptors 30 on a single sensing electrode 30 can be easily detected by the fact that in the presence of more than one suitable analyte of interest being present in the sample, multiple binding events are likely to take place at the sensing electrode, thus leading to a sensor signal that is an aggregation of the electrical signatures of the beads 60 involved in these binding reactions. This sensor signal may be decomposed into its individual components using known mathematical principles. Alternatively, the various binding events may be detected in the frequency domain using a signal modulation technique that will be explained in more detail below with the aid of FIG. 21-23.

Figure 11:
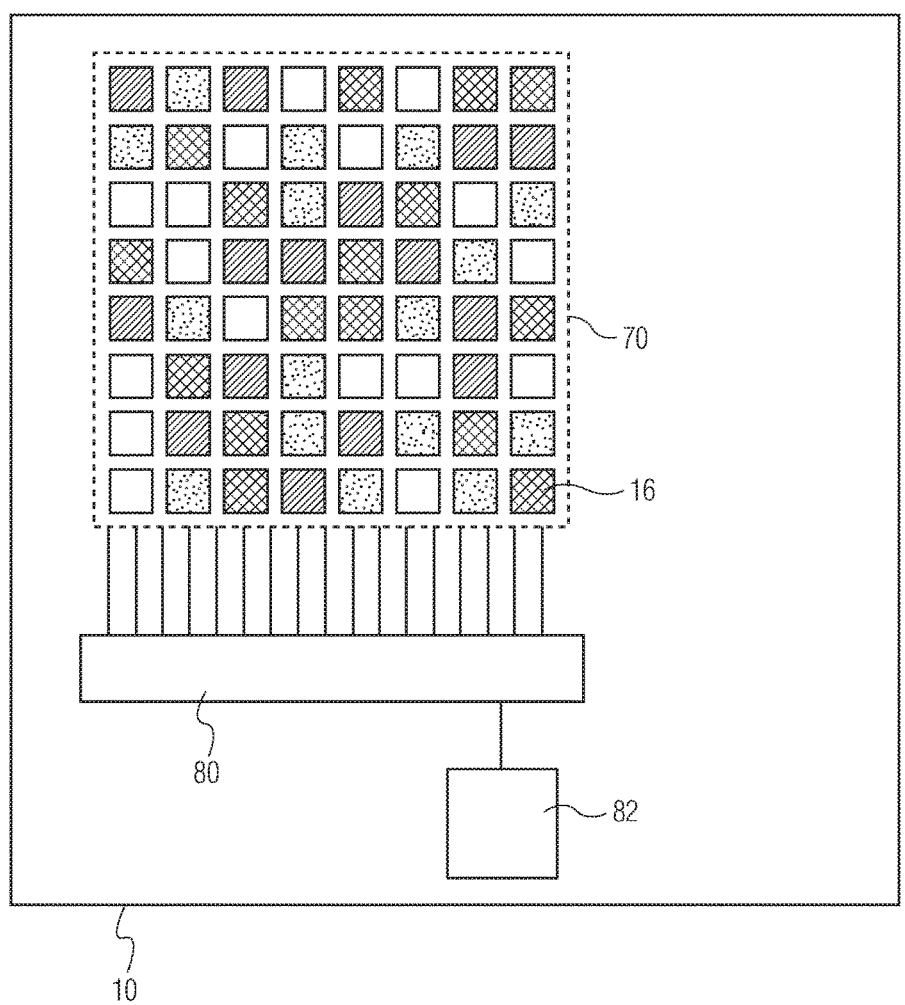

FIG. 11 shows an embodiment of an IC of the present invention in more detail. The IC 10 comprises a sensor array 70 comprising a plurality of sensing elements that each include a separate sensing electrode 16 at an exposed surface of the IC 10. The sensing electrodes 16 may be functionalized as described above. Alternatively, the sensing electrodes 16 may be functionalized using well-known spotting techniques. The IC 10 further comprises a signal processor 80 that is individually connected to the sensing elements of the sensing array 70. The signal processor 80 is configured to detect a electrical signature of a bead 60 on each of the sensing elements including respective sensing electrodes 16. To this end, the signal processor may for instance have access to a memory 82, e.g. a look-up table, in which a plurality of predefined electrical signatures may be stored together with the analyte of interest assigned to that signature.

In operation, the signal processor 80 may compare a detected electrical signature with the stored electrical signature and upon a match, produce an output signal indicative of the detection of the analyte of interest assigned to the electrical signature stored in the memory 82. The signal processor 80 may be further configured to count the number of detections of a particular analyte of interest, e.g. by counting the number of positive matches of the electrical signature of its associated bead and provide this number as an indication of the concentration of the analyte of interest in the tested sample.

The IC 10 may for instance form part of a sensor device (not shown) comprising a flow channel in which the sensing array 70 is exposed, wherein during a typical measurement a sample that may contain at least one of the analytes of interest is fed through the flow channel, thereby bringing the sensing array 70 into contact with the sample. A subsequent rinsing step may be applied to remove any unreacted analyte of interest and, in particular, any unbound beads to avoid such beads contaminating the sensing array 70 and corrupting the electrical signatures of the beads bound to the respective sensing electrodes 16.

Figure 12:
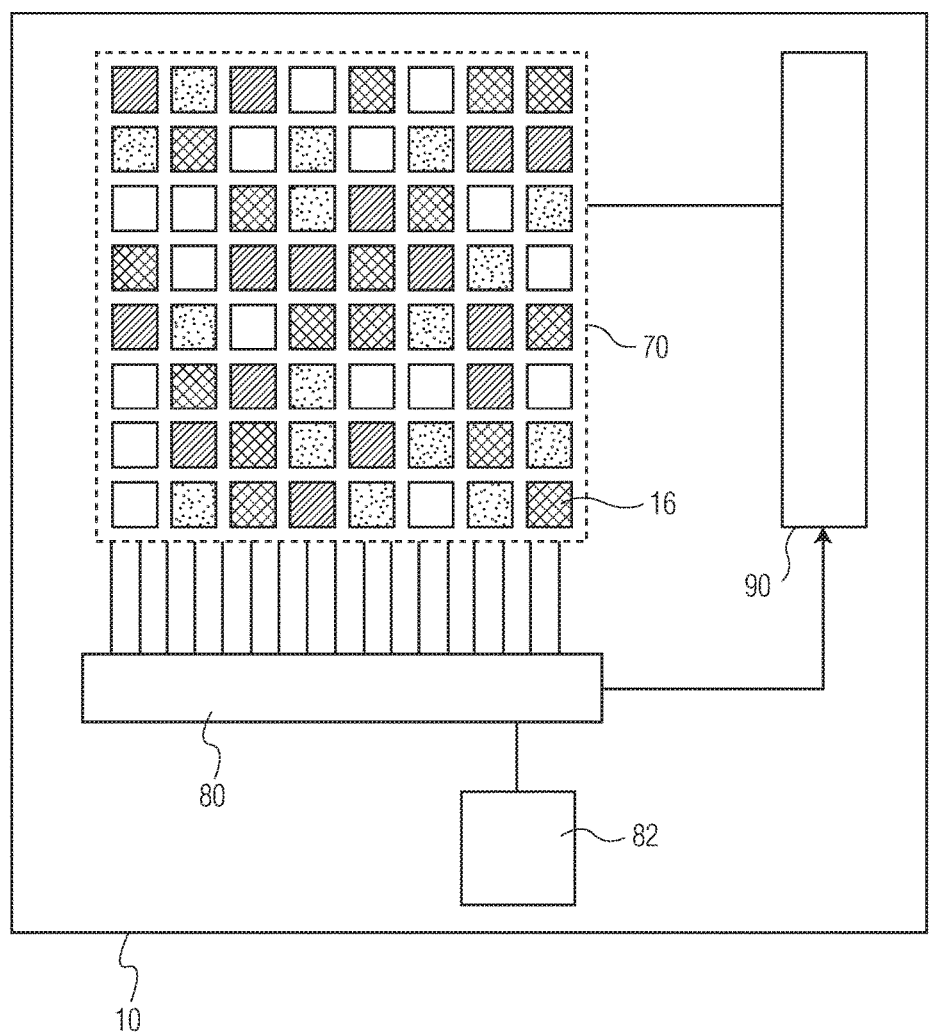

Upon returning to FIG. 11, it is noted that so far, the detection of the electrical signature has been explained in terms of a change in the magnitude or amplitude of the capacitance detected by the respective sensing electrodes 16. However, it is equally feasible to detect the electrical signature in the frequency domain. An embodiment of an IC configured to detect the electrical signature in the frequency domain is shown in FIG. 12. In addition to the features already shown in FIG. 11, the IC 10 further comprises an electromagnetic field generator 90, which is adapted to subject the sensing array 80 to an oscillating electromagnetic field having a variable frequency f. In this embodiment, the various beads 60 should be conductive and/or magnetic beads.

Figure 13:
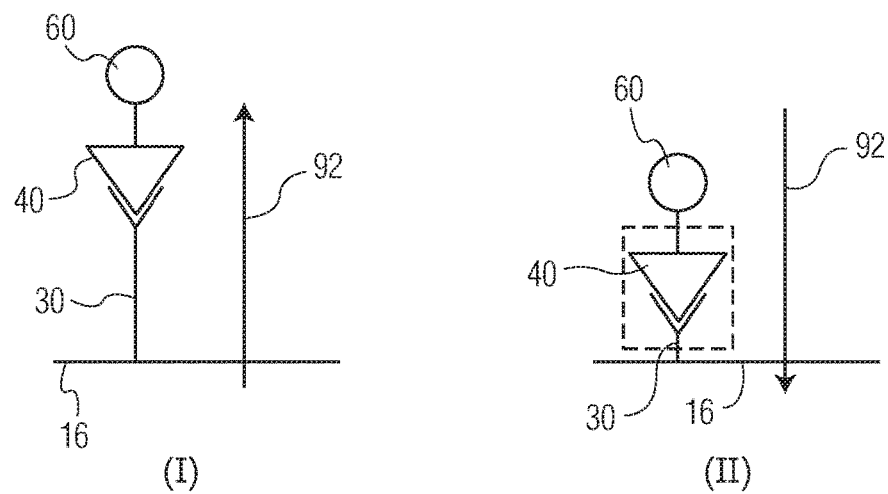

In operation, the electromagnetic field generator 90 subjects the sensing array 80 to an electromagnetic field of a continually increasing or decreasing frequency, i.e. an electric or magnetic field in which the field polarity is rotated at this frequency. This causes a bead 60 to oscillate in the applied electromagnetic field, as shown in FIG. 13. In pane (I), the electromagnetic field 92 has a repulsive effect on the bead 60, thus forcing it away from the surface of the sensing electrode 16, whereas half a period later, the electromagnetic field 92 has an attractive effect on the bead 60, thus forcing it towards the surface of the sensing electrode 16.

This periodic displacement, which is facilitated by the conformational flexibility in the specific binding pair formed by the receptor molecule 30, the analyte of interest 40 and a further molecule such as a further antibody in a sandwich assay, causes a modulation of the sensing signal detected by the sensing element comprising the sensing electrode 16 with the frequency of the oscillating electromagnetic field 92.

Depending on the size of the bead 60, the motional or displacement resistance will vary. For each bead 60, there will be a critical oscillating frequency above which the bead is unable to follow the applied electromagnetic field 92 as the viscous drag in the (sample) fluid prohibits the bead 60 to follow this field.

This cut-off frequency is directly related to the dimensions of the bead 60. In other words, different size beads 60 will exhibit different cut-off frequencies, such that the determination of the cut-off frequency of a bead having a particular size can be used to detect the presence of an analyte of interest associated with that bead. To this end, the signal processor 80 is adapted to determine the field frequency at which a modulation of a capacitive signal detected by a particular sensing element disappears, and to compare this cut-off frequency with the cut-off frequencies stored in the memory 82 together with the associated analytes of interest. The signal processor 80 may further be adapted to control the electromagnetic field generator 90.

Figure 14:
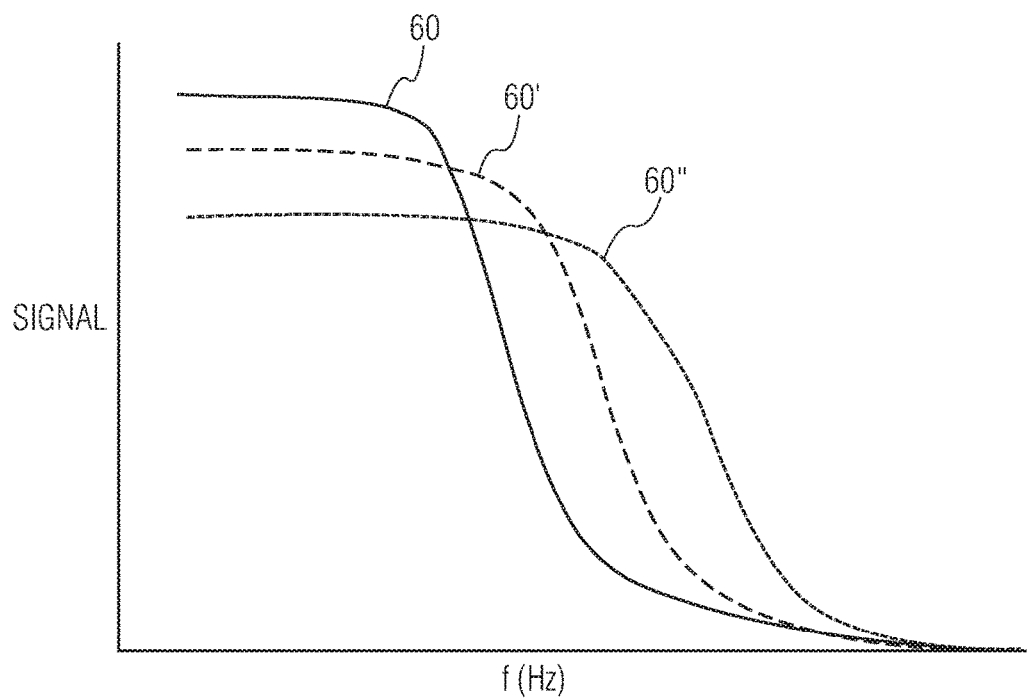

The effect of the cut-off frequency on the signal modulation generated for three different size beads is schematically shown in FIG. 14. Bead 60 is the largest bead and bead 60" is the smallest bead, with bead 60' having an intermediate size. It will be immediately apparent that for such different size beads, different cut-off frequencies are obtained.

The proof of concept of the present invention will now be demonstrated in more detail by way of the following experimental examples. It will be appreciated that this examples have been selected for illustrative purposes only and that they should be not be construed to limit the scope of the invention in any manner.

Figure 15:
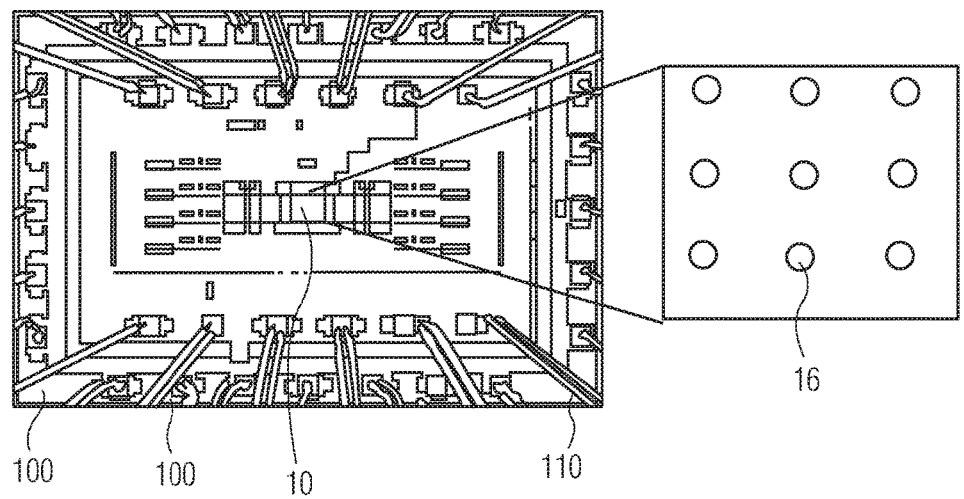
FIG. 15 is a microscopic image of an example biosensor according to the present invention.

FIG. 15 depicts a microscopic image of a biosensor comprising an integrated circuit 10 according to an embodiment of the present invention. The IC 10 comprises a regular 256×256 array of 65,536 circular gold electrodes 16 each having a diameter of 130 nm, as demonstrated by the blown-up portion of the image at the right-hand side of FIG. 15. The sensor electrodes 16 are connected to a pair of serially connected transistors essentially as disclosed in WO 2009/047703, and in particular as shown in FIG. 1 of this application. In FIG. 15, the IC 10 is mounted on a carrier 100 with exposed connections 110. It will be appreciated that this is for the sake of clarity only, and that the connections 110 are typically covered by a molding to prevent short circuits when the IC 10 is exposed to a fluid sample.

The biosensor shown in FIG. 15 has been used in the following experiment.

Experiment 1

The IC 10 of the biosensor was exposed to a 10 mM phosphate buffered solution (PBS). After the initial exposure to the PBS solution, the IC 10 was exposed to deionized water (mQ grade) for 10 minutes, followed by a 10 minute exposure to a 10 mM PBS solution. This was followed by exposure to a 10 mM PBS solution comprising polystyrene beads comprising iron grains. The beads have a 500 nm diameter. Finally, the IC 10 was exposed to a 10 mM PBS solution for a further 10 minutes.

Experiment 2

In this experiment, the IC 10 was exposed to the same sequence of solutions as in experiment 1, with the difference that beads having a 119 nm diameter were used.

Figure 16:
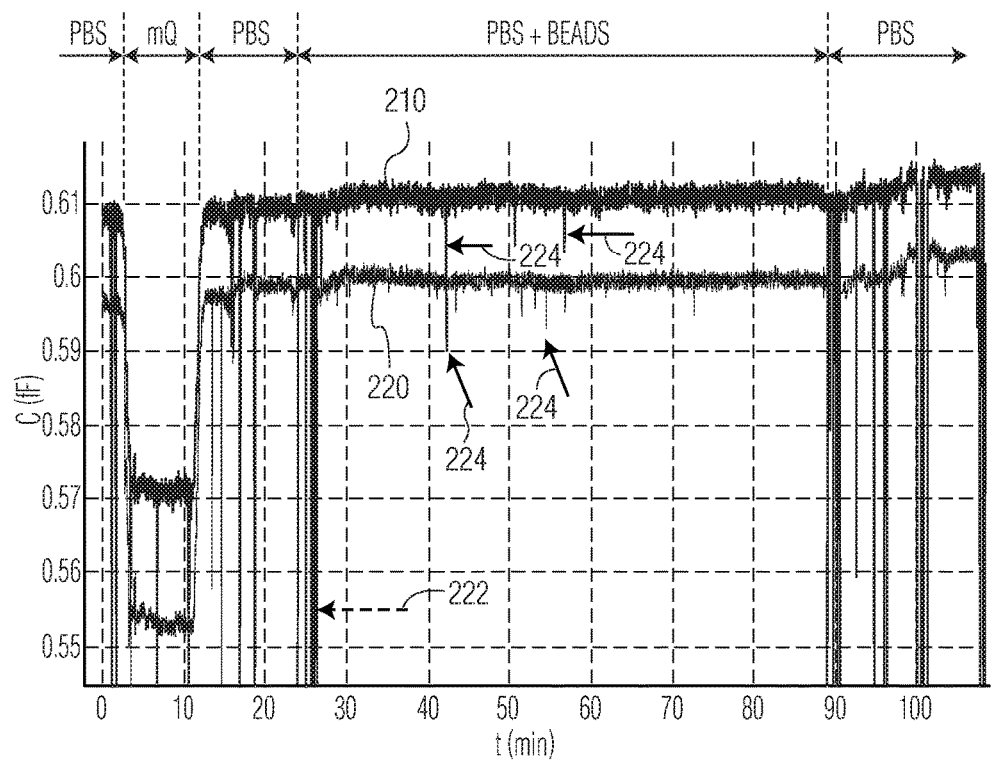
FIG. 16-20 depict various signal traces of electrodes obtained with the biosensor of FIG. 15.

FIG. 16 depicts the measurement signals 210 and 220 of two electrodes 16 of the IC 10 as obtained during experiment 1. As can be seen, upon replacing the PBS solution with the deionized water solution labeled mQ in FIG. 15, a large drop in capacitance of the capacitance sensor is observed, which is caused by the different dielectric and conductive properties of the deionized water compared to the PBS solution. The large drops in capacitance that can be observed and that are indicated by the dashed arrow 222 are caused by the passage of air bubbles over the electrodes 16. This causes the dielectric constant of the medium over the electrodes 16 to temporarily approach 1, which reduces the capacitance of the capacitor including the electrode 16 as is well-known.

Upon replacing the deionized water with a PBS solution, the capacitance of the capacitor including the electrode 16 again increases. Once the beads are added to the PBS solution, downward spikes in the measured capacitance are clearly noticeable, as indicated by the solid arrows 224 in FIG. 15. This drop in capacitance is caused by an electrically insulating bead travelling over the sensing electrode 16. It will be understood that the size of the spike depends on the overlap of the bead with the sensing electrode 16 as well as the distance of the bead to the sensing electrode 16, amongst others. It is important to observe that it is clearly demonstrated by the signal traces 210 and 220 that during the PBS+BEADS period, the bead signals are clearly much stronger than the typical noise levels in these signals.

Figure 17:
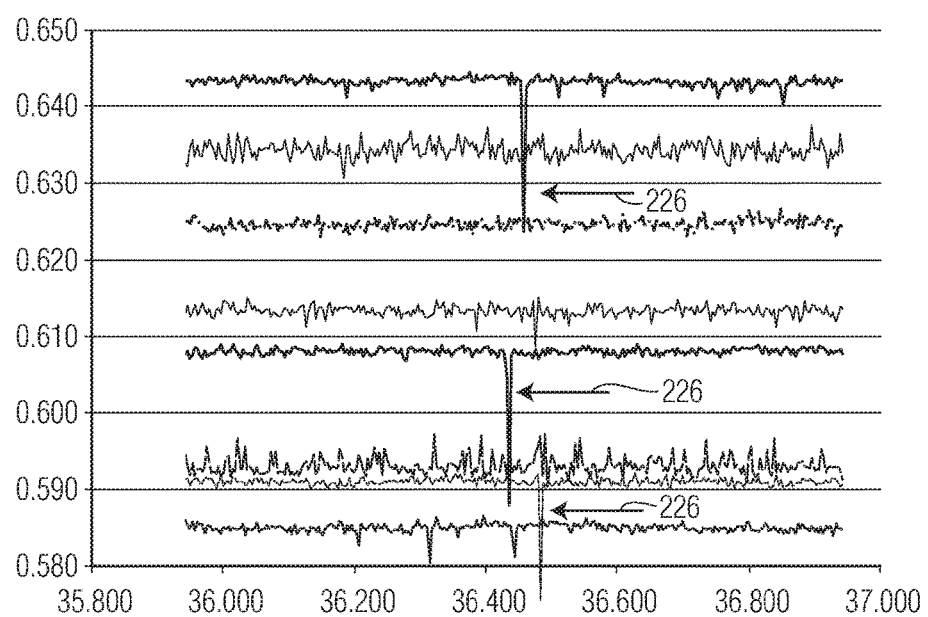

FIG. 17 depicts a part of the PBS+BEADS time period of FIG. 16 in more detail for a number of signal traces of different electrodes 16. Here, it can be clearly recognized as indicated by the solid arrows 226 that beads passing one of the electrodes 16 cause a distinct drop in the capacitance of the capacitor comprising the sensing electrode 16 as one of its plates.

Figure 18:
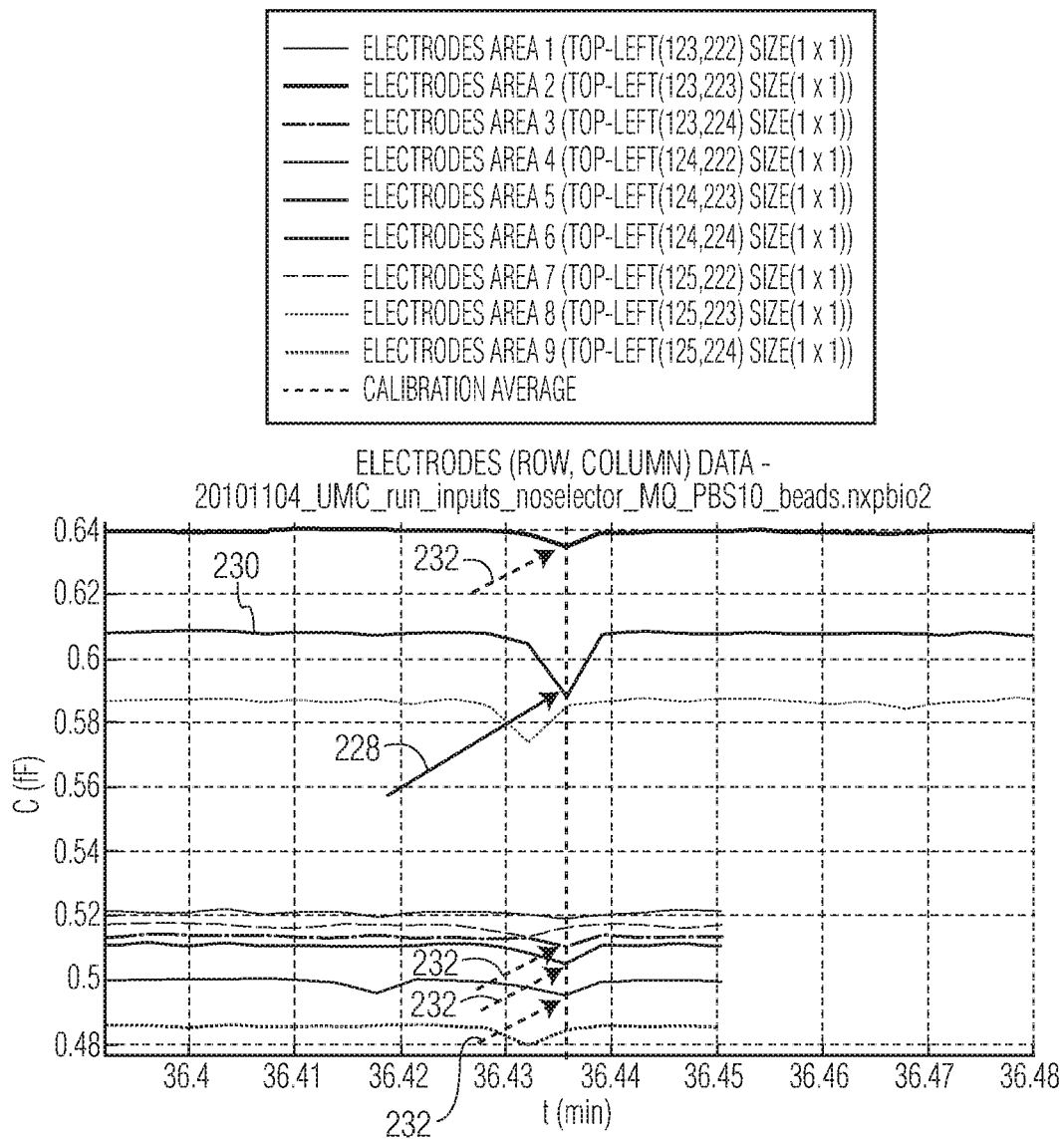

Further evidence that a single electrode 16 of the IC 10 is capable of detecting a single bead can be derived from FIG. 18, which depicts a signal trace 230 of a 130 nm gold electrode 16 of the IC 10 in FIG. 15. As indicated by the solid arrow 228, a drop in capacitance is attributed to an electrically insulating bead passing the surface of the gold electrode 16 in close enough vicinity such that the 500 nm diameter bead is detected by the gold electrode 16. However, it will be appreciated that the bead has a significantly larger diameter than the gold electrode 16. As the spacing between the gold electrodes 16 of the IC is around 300 nm, this means that this bead must also partially overlap with the neighboring gold electrodes, which should trigger a detection signal of smaller magnitude in the signal traces of these surrounding electrodes at the same time as the main detection event. Such secondary detection events can indeed be observed as indicated by the dashed arrows 232 in FIG. 18.

Figure 19:
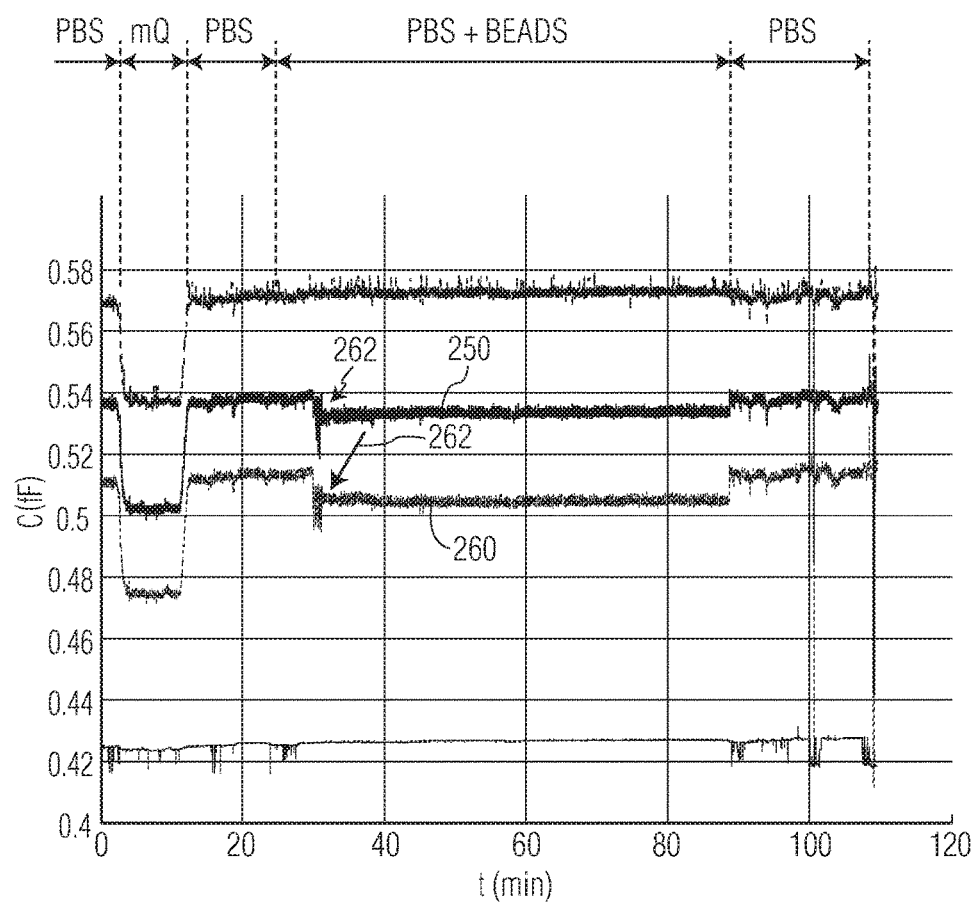

FIG. 16-18 provide evidence of the detection of beads that pass over the surface of the IC 10. FIG. 19 provides evidence that a bead can be detected whilst stationary on the surface of an electrode 16. A number of signal traces of individual gold electrodes 16 of IC 10 as obtained during experiment 1 are shown, including signal traces 250 and 260 As indicated by the solid arrows 262, the signal traces 250 and 260 depict a noticeable drop in capacitance during the PBS+BEADS cycle of experiment 1, which reduction is reversed during the subsequent PBS rinsing cycle. This continued drop in capacitance observed in signal traces 250 and 260 is attributed to a bead adhering to the surface of the corresponding gold electrode 16. It can be seen that during the adhesion of the bead to the electrode surface, no (further) single bead events can be observed. It is noted for the sake of completeness that the mechanism behind the adhesion of these beads onto the gold surface of the electrodes 16 is not fully understood.

Figure 20:
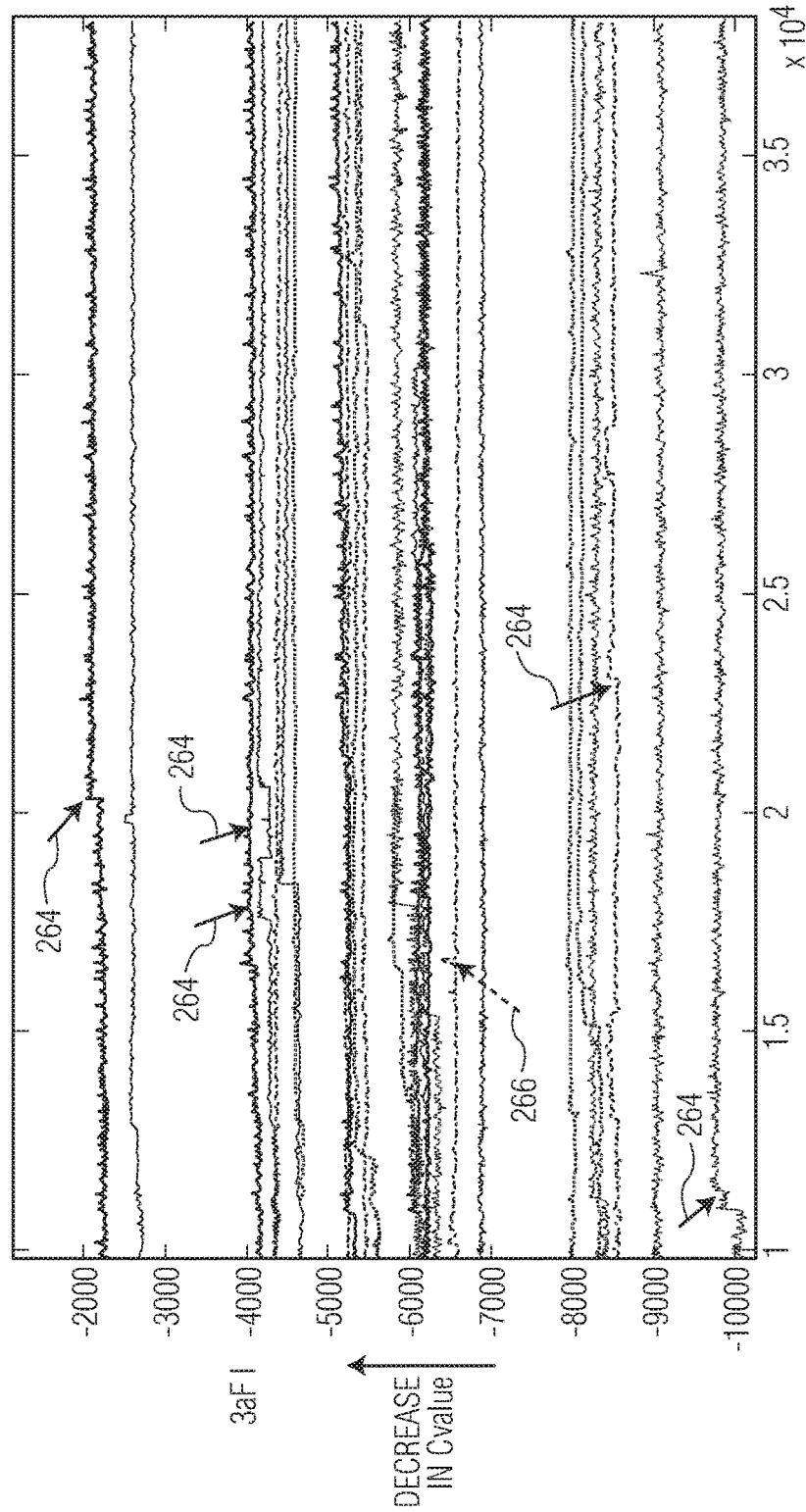

FIG. 20 depicts a plurality of signal traces of respective individual electrodes 16 as obtained during experiment 2, in which 119 nm electrically insulating beads were used instead of the 500 nm beads of experiment 1. The PBS+BEADS cycle of this experiment is shown in FIG. 20 The solid arrows 264 indicate bead adhesion events detected by the gold electrodes 16 and the dashed arrow 266 indicates a bead passing a gold electrode 16. It is noted for the sake of clarity that the Y-axis of FIG. 20 shows a decrease in capacitance rather than capacitance such that the bead detection events in FIG. 20 are depicted as a positive change in the signal traces. More particularly, the Y-axis displays an A/D converter code, with an increase in this code corresponding to a decrease in the measured capacitance.

FIG. 21 schematically depicts a preferred embodiment of a control signal 300 of an electrode 16 of the IC 10. The control signal 300 comprises a first modulation, which typically is a high-frequency modulation typically in the MHz domain, and a second modulation, which is indicated by the dashed lines in FIG. 21, which is of a much lower frequency than the first modulation and is typically in the kHz domain. The modulation frequencies of the control signal 300 are shown in FIG. 22 The high frequency modulation is used to improve the resolution of the capacitance measurement, as it is known per se that small capacitances can be accurately measured using high frequency modulated signals.

The purpose of the second frequency modulation will now be explained in more detail. As a bead such as bead 60 is attached to the surface of the electrode 16 via one or more (bio)-molecules, the bead 60 will attempt to follow the modulation in the control signal 300, as this modulation causes an electrical field above the electrode 16 modulated with the first and second modulation frequencies. The first (high) frequency modulation is much too high for the bead 60 or 60' being able to respond to this modulation, as the viscous drag of the medium in which the bead 60 is suspended is too high to allow the bead 60 to follow this modulation.

However, the critical response frequency of a bead 60 having nm dimensions typically lies in the kHz domain. The critical response frequency is the maximum modulation frequency that the bead 60 can follow. As the critical response frequency is dominated by the physical properties of the bead 60, most notably its dimensions, different size beads 60 will exhibit different critical response frequencies, as is indicated in FIG. 23 by arrows 400. To this end, the control circuitry of the IC 10 may be adapted to perform a signal sweep for the control signal 300 in which the frequency of the second (lower frequency) modulation is systematically varied from a first frequency value to a second frequency value, either in discrete steps or continuously.

As long as the second modulation frequency of the control signal 300 remains below the critical response frequency of a particular bead 60, the electrode 16 will produce a capacitance signal that is modulated with the second modulation frequency as the bead 60 is capable of following the induced variations in the electric field, i.e. the bead 60 is capable of oscillating with the applied electric field, thus causing a modulated variation in the capacitance of the capacitor comprising the electrode 16.

However, as soon as the second modulation frequency of the control signal 300 exceeds the critical response frequency of a particular bead 60, the modulation of the signal detected by the electrode 16 will disappear as the bead no longer can follow the variations in the direction of the electric field, i.e. becomes stationary, such that the modulations in the capacitance value of the capacitor including the electrode 16 will disappear. As the different beads 60 typically have different critical response frequencies, the binding event of a particular bead 60 on an electrode 16 can simply be detected by the determination of its critical response frequency.

This also makes it possible to detect simultaneous binding events of different analytes of interest on a single electrode 16, as each binding event can be recognized by the unique critical response frequency of its associated bead, such that multiple binding events can be readily detected in a single frequency sweep of the second modulation frequency.

Finally, it is stipulated that the methods and IC of the present invention are suitable for are suitable for all known biological affinity reactions involving specific binding events, e.g. DNA, proteins, aptamers, membrane proteins binding reactions and so on. It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. The word "comprising" does not exclude the presence of elements or steps other than those listed in a claim. The word "a" or "an" preceding an element does not exclude the presence of a plurality of such elements. The invention can be implemented by means of hardware comprising several distinct elements. In the device claim enumerating several means, several of these means can be embodied by one and the same item of hardware. The mere fact that certain measures are recited in mutually different dependent claims does not indicate that a combination of these measures cannot be used to advantage.

The invention claimed is:

1. An apparatus comprising:
   a functionalized integrated circuit, the functionalized integrated circuit including:
   an array of individually addressable sensor devices, the sensor devices including nano electrodes;
   a random distribution of receptor molecules on the nano electrodes of the respective sensor devices, wherein at least a first sensing device includes a first nano electrode having at its surface a first receptor molecule for selectively binding to a first analyte of interest and a second receptor molecule for selectively binding to a second analyte of interest;
   a sample comprising at least one of the first analyte of interest and the second analyte of interest;
   a first bead having a first electrical signature attached to a first molecule having a conformation or an affinity for binding to the first nano electrode that is dependent on the presence of the first analyte in the sample;
   a second bead having a second electrical signature, which is different from the first electrical signature, attached to a second molecule having a conformation or an affinity for binding to the first nano electrode that is dependent on the presence of the second analyte in the sample;
   a signal processor individually coupled to the respective sensor devices, the signal processor being configured to identify a specific binding event of a particular analyte of interest on said first nano electrode of said first sensor device based on a detected electrical signature of a particular bead involved in said binding event, wherein said particular bead is one of the first bead and the second bead, wherein said signal processor has access to a memory for storing predefined electrical signatures including the first electrical signature and the second electrical signature, and wherein the signal processor is configured to compare the detected electrical signature to the predefined electrical signatures to identify the specific binding event.

2. The apparatus of claim 1, the functionalized integrated circuit further comprising a field generator for applying an oscillating electromagnetic field having a time-variable frequency to the array of sensor devices, wherein the signal processor is configured to identify an analyte of interest by way of the resonance characteristics in said oscillating electromagnetic field of the particular bead involved in the binding reaction of said analyte of interest.

3. The apparatus of claim 2, wherein the field generator is configured to generate an oscillating electromagnetic field having a time-variable frequency in which the field polarity is rotated at said time-variable frequency.

4. The apparatus of claim 2, wherein a difference between a first resonance characteristic of the first bead and a second resonance characteristic of the second bead corresponds to a difference between a first size of the first bead and a second size of the second bead.

5. The apparatus of claim 4, wherein the first resonance characteristic comprises a first cut-off frequency and the second resonance characteristic comprises a second cut-off frequency.

6. The apparatus of claim 1, wherein the nano electrodes have a dimension of less than 300 nm.

7. The apparatus of claim 6, wherein the individually addressable sensor devices are composed of CMOS technology.

8. The apparatus of claim 1, wherein the detected electrical signature matches the first electrical signature of the first bead, which indicates that the specific binding event involves the first analyte of interest selectively binding to the first receptor molecule, wherein the first molecule selectively binds to the first analyte of interest.

9. The apparatus of claim 1, wherein the detected electrical signature matches the first electrical signature of the first bead, which indicates that the specific binding event involves the first analyte of interest selectively binding to the first receptor molecule, wherein the first molecule was initially selectively bound to the first receptor molecule and is expelled by the first analyte of interest.

10. The apparatus of claim 1, wherein the detected electrical signature matches the first electrical signature of the first bead, which indicates that the specific binding event involves the first analyte of interest selectively binding to the first receptor molecule, wherein the first molecule was initially selectively bound to the first receptor molecule in a first conformation that provides a first capacitance, and the first receptor molecule changes to a second conformation that provides a second capacitance when selectively bound to the first analyte of interest.

11. The apparatus of claim 10, wherein the first conformation is a folded conformation that positions the first bead at a first distance from the surface of the first nano electrode, and the second conformation is an unfolded conformation that position the first bead at a second distance from the surface of the first nano electrode, wherein the second distance is greater than the first distance.

12. The apparatus of claim 1, wherein a difference between the first electrical signature and the second electrical signature corresponds to a difference between a first size of the first bead and a second size of the second bead.

13. The apparatus of claim 1, wherein a difference between the first electrical signature and the second electrical signature corresponds to a difference between a first dielectric constant of the first bead and a second dielectric constant of the second bead.

14. The apparatus of claim 1, wherein a difference between the first electrical signature and the second electrical signature corresponds to a difference between a first material of the first bead and a second material of the second bead.

15. An apparatus comprising:
a functionalized integrated circuit including;
a plurality of individually addressable sensing electrodes;
a random distribution of receptor molecules on the respective sensing electrodes, wherein at least a first sensing electrode includes at its surface a first receptor molecule for selectively binding to a first analyte of interest and a second receptor molecule for selectively binding to a second analyte of interest;
a sample comprising at least one of the first analyte of interest and the second analyte of interest;
a first bead having a first electrical signature attached to a first molecule having a conformation or an affinity for binding to the first sensing electrode that is dependent on the presence of the first analyte in the sample;
a second bead having a second electrical signature, which is different from the first electrical signature, attached to a second molecule having a conformation or an affinity for binding to the first sensing electrode that is dependent on the presence of the second analyte in the sample; and
a signal processor individually coupled to the respective electrodes, the signal processor being configured to identify a specific binding event of a particular analyte of interest on said sensing electrodes based on a detected electrical signature of a particular bead involved in said specific binding event, wherein the detected electrical signature is an aggregation of a plurality of electrical signatures of instances of the particular bead detected by said sensing electrodes, which includes the first sensing electrode; and
wherein the signal processor has access to a memory for storing predefined electrical signatures including the first electrical signature and the second electrical signature, and wherein the signal processor is configured to compare the detected electrical signature to the predefined electrical signatures to identify the specific binding event.

16. The apparatus of claim 15, further comprising a field generator for applying an oscillating electromagnetic field having a time-variable frequency to the plurality of sensing electrodes;
wherein the signal processor is configured to identify an analyte of interest by way of the resonance characteristics in said oscillating electromagnetic field of the bead involved in the binding reaction of said analyte of interest, wherein the field generator is configured to generate an oscillating electromagnetic field having a time-variable frequency in which the field polarity is rotated at said time-variable frequency.

17. An apparatus comprising:
a row and column array of individually addressable sensor devices, the sensor devices including nano electrodes and wherein a capacitor is formed at the sensor devices by the corresponding nano electrode and an analyte of interest, which are separated by a dielectric layer formed by one or more capture molecules; and
a random distribution of receptor molecules on the respective nano electrodes, wherein at least a first nano electrode includes at its surface a first receptor molecule for selectively binding to a first analyte of interest and a second receptor molecule for selectively binding to a second analyte of interest;
a sample comprising at least one of the first analyte of interest and the second analyte of interest;
a first bead having a first capacitance signature attached to a first molecule having a conformation or an affinity for binding to the first nano electrode that is dependent on the presence of the first analyte in the sample;
a second bead having a second capacitance signature, which is different from the first capacitance signature, attached to a second molecule having a conformation or an affinity for binding to the first nano electrode that is dependent on the presence of the second analyte in the sample; and
a signal processor individually coupled to the respective sensor devices, the signal processor being configured to identify a specific binding event of a particular analyte of interest on said first nano electrode of said first sensor device based on a detected capacitance signature of a particular bead involved in said binding event, wherein said particular bead is one of the first bead and the second bead, wherein the detected capacitance signature is a function of the size of the particular bead, wherein said signal processor has access to a memory for storing predefined capacitance signatures including the first capacitance signature and the capacitance electrical signature, and wherein the signal processor is configured to compare the detected capacitance signature to the predefined capacitance signatures to identify the specific binding event.

18. The apparatus of claim 17, wherein a capacitance change is directly proportional to the volume of the bead and its dielectric properties.

19. The apparatus of claim 17, wherein the nano electrodes have a dimension of less than 300 nm.

20. The apparatus of claim 19, wherein the individually addressable sensor devices are composed of CMOS technology.

* * * * *